United States Patent [19]

Van Dedem et al.

[11] Patent Number: 5,164,377
[45] Date of Patent: Nov. 17, 1992

[54] SULPHATED GLYCOSAMINOGLYCURONAN WITH ANTITHROMBOTIC ACTIVITY

[75] Inventors: Gijsbert W. K. Van Dedem, Oss; François E. A. Van Hou Denhoven, Heesch; Dirk G. Meuleman, Oss; Huibert C. T. Moelker, Megen; Adrianus L. M. Sanders, Uden, all of Netherlands

[73] Assignee: Akzo N.V., Arnhem, Netherlands

[21] Appl. No.: 592,152

[22] Filed: Oct. 3, 1990

[30] Foreign Application Priority Data

Oct. 4, 1989 [EP] European Pat. Off. ........ 89202494.4

[51] Int. Cl.⁵ .................. A61K 31/725; C08B 37/00; C08B 37/08
[52] U.S. Cl. ........................ 514/54; 536/54; 536/55; 536/55.1; 536/55.3; 536/124; 536/127
[58] Field of Search ............... 536/54, 55, 55.1, 124, 536/21, 127, 55.3; 514/54, 56

[56] References Cited

U.S. PATENT DOCUMENTS

| | | | |
|---|---|---|---|
| 3,887,703 | 6/1975 | Manoussos et al. | 514/54 |
| 3,936,351 | 2/1976 | Bianchini | 536/54 |
| 4,438,108 | 3/1984 | Sanders et al. | 514/54 |
| 4,489,066 | 12/1984 | Fedeli | 536/1.1 |
| 4,745,098 | 5/1988 | Michaeli | 514/54 |
| 4,783,447 | 11/1988 | Del Bono et al. | 514/56 |
| 4,987,222 | 1/1991 | De Ambrosi et al. | 514/54 |
| 5,008,253 | 4/1991 | Casu et al. | 536/54 |
| 5,013,724 | 5/1991 | Petitou et al. | 536/54 |

FOREIGN PATENT DOCUMENTS

| | | | |
|---|---|---|---|
| 0011322 | 5/1980 | European Pat. Off. | 514/54 |
| 0199033 | 10/1986 | European Pat. Off. | |
| 1492017 | 2/1969 | Fed. Rep. of Germany | 536/127 |
| 0136572 | 7/1979 | Fed. Rep. of Germany | 514/54 |
| 3244214 | 5/1984 | Fed. Rep. of Germany | |
| 51-51509 | 5/1976 | Japan | 514/54 |

OTHER PUBLICATIONS

Harada et al.; Chemical Abstracts 85:68276e (1976).
Casu et al.; Arzneim.-Forsch./Drug Res. 30 (II), Nr. 11 pp. 1889-1892 (1980).
Maggi et al.; Haemostasis 17:329-335 (1987).
Nusimovich et al.; Chemical Abstracts 110:170974c (1989).
Pharmalogical Research Communications, vol. 11, No. 4, pp. 297-310 (1979).

*Primary Examiner*—Ronald W. Griffin
*Assistant Examiner*—Nancy S. Carson
*Attorney, Agent, or Firm*—William M. Blackstone

[57] ABSTRACT

The present invention relates to sulphated glycosamino glycuronan with antithrombotic activity consisting essentially of salts of dermatan sulphate, chondroitin sulphate and heparan sulphate, characterized by
a) an average molecular weight between 4000 and 8000 daltons;
b) a nitrogen content between 2.4 and 3.0%;
c) a sulphur content between 7.5 and 9.5%;
d) a sodium content between 9 and 11%;
e) a dermatan sulphate content between 5 and 25%;
f) a chondroitin sulphate content less than 9%;
g) an anti-Xa activity between 11 and 20 μ/mg; and
h) an antithrombin III dependent antithrombin activity of less than 1 μ/mg.

4 Claims, No Drawings

SULPHATED GLYCOSAMINOGLYCURONAN WITH ANTITHROMBOTIC ACTIVITY

The present invention relates to sulphated qlycosamino glycuronan with antithrombotic activity, its process of manufacture and pharmaceutical compositions containing the same.

Sulphated glycosaminoglycuronans with antithrombotic activity are known from U.S. Pat. No. 4,438,108. The instantly claimed products of said patent are assumed to have minimal haemorrhagic activity, which is of utmost importance, because haemorrhagic activity renders such products unsuitable for use in humans.

The haemorrhagic activity of these products has been determined by means of the muscle bleeding test and the capillary bleeding test in rats.

However, we discovered that these tests are too insensitive to predict haemorrhagic activity in humans, and indeed in clinical safety studies most of the products of U.S. Pat. No. 4,438,108 enhanced bleeding, especially showed prolonged bleeding times, which is severe enough to be prohibitive for further clinical development. We have now found that a new process for the manufacture of sulphated glycosaminoglycuronan, comprising a preliminary separation of heparin and the product of this invention by ultrafiltration, followed by further purification of the latter by fractional elution from ion exchanger and methanol fractionation, affords a new product having a different chemical composition, and showing a considerably improved pharmacological and clinical profile, especially with regard to the bleeding enhancing properties.

The major physico-chemical difference of this new product compared with the prior art product is the sulphur content between 7.5 and 9.5%, and preferably between 8.0 and 8.5%, which is substantially higher than in the prior art product.

Surprisingly, the higher sulphur content is accompanied with a reduced bleeding risk, contrary to what might be expected. Generally, it has been assumed that a higher sulphur content increases the bleeding risks for this type of compounds (see e.g. J. Van Ryn-McKenna et al., Antithrombotic and bleeding effects of glycosaminoglycans with different degrees of sulphation, Br. J. Haem., (1989), 71, 265-269). Moreover, the new product shows less systemic side effects than the prior art compound.

The invention comprises sulphated glycosaminoglycuronans with antithrombotic activity consisting essentially of salts, with a preference for sodium salts, of dermatan sulphate, chondroitin sulphate and heparan sulphate, characterized by a) an average molecular weight between 4000 and 8000 daltons;
b) a nitrogen content between 2.4 and 3.0%;
c) a sulphur content between 7.5 and 9.5%;
d) a sodium content between 9 and 11%;
e) a dermatan sulphate content between 5 and 25%;
f) a chondroitin sulphate content less than 9%;
g) an anti-Xa activity between 11 and 20 u/mg; and
h) an antithrombin III dependent antithrombin activity of less than 1 u/mg.

The heparan sulphate component of the product may be heparan sulphate with or without affinity to antithrombin III, as well as mixtures of low and high affinity heparan sulphate. Minor quantities of sulphated glycosaminoglycuronans with a molecular weight greater than 10,000 daltons may be present. The bleeding risk of the new product was compared with that of the prior art compound in different studies after single dose i.v. bolus injections in healthy young male volunteers. The major safety parameter examined was the increase of bleeding time ($\Delta BT$) performed using the Simplate ® II device but using a slightly modified technique which involved pressing the device onto the forearm to gain maximum skin/cutting blade contact. The result which is depicted in Table I, allows differentiation between batches of the prior art product and batches of the new product, which appear to parallel changes in relative glycosaminoglycuronan composition as a consequence of alterations in the isolation procedure.

TABLE I

| Treatment I.V. | No. of volunteers | Dose anti-Xa u | Mean anti-Xa activity | % of volunteers with $\Delta BT$ | | |
|---|---|---|---|---|---|---|
| | | | | >5 min | >10 min | >15 min |
| Heparin | 10 | 5000 | | 80 | 80 | 40 |
| prior art | 6 | 1600 | 10 u/mg | 50 | 17 | 17 |
| (USP 4,438,108) | 16 | 3200 | 10 u/mg | 44 | 31 | 7 |
| (3 batches) | 13 | 6400 | 10 u/mg | 85 | 62 | 56 |
| this | 8 | 1600 | 14.2 u/mg | 13 | 0 | 0 |
| invention | 64 | 3200 | 14.2 u/mg | 25 | 9 | 3 |
| (6 batches) | 28 | 6400 | 14.2 u/mg | 36 | 25 | 8 |

The clinical differences as demonstrated in Table I can also be shown pharmacologically by the sensitive subdermal bleeding test. The bleeding is measured by evaluating the haemoglobin concentration, using the analysis for a randomized block design, and expressed as the percentage geometric mean concentration of the haemoglobin concentration after administration of the compound:geometric mean concentration of the haemoglobulin concentration after administration of vehicle $\times 100$. The haemoglobin concentration is a measure for the blood loss, and is determined on i.v. administration in rats of 100, 200, 400 and 800 u/kg of the compound. The results are expressed as a curve of this percentage against the dose, after which the area under the curve (AUC) can be calculated. The AUC values are depicted in Table II for Heparin USP (as reference), 5 batches (A-E) of the prior art product and for 4 batches (I-IV) of the new product (see examples).

TABLE II

| | batch | AUC $\times 10^3$ | mean |
|---|---|---|---|
| Heparin USP | — | >210 | — |
| prior art | A | 252 | 205 |
| (USP 4,438,108) | C | 196 | |
| | D | 256 | |
| | E | 189 | |
| this | I | 125 | 133 |
| invention | II | 91 | |

TABLE II-continued

| batch | AUC × 10³ | mean |
|---|---|---|
| III | 151 | |
| IV | 166 | |

Because of the strongly reduced bleeding risks the new product is pre-eminently suitable for the prophylaxis and treatment of venous thrombosis, thromboembolism and deep vein thrombosis. Moreover the product has anti-allergic, anti-inflammatory and anti-atherosclerotic activity.

The new product can be obtained by autolysis or proteolysis (e.g. enzymes from pig pancreas or bacterial enzymes, such as proteases from Bacillus subtilis) of mammal tissue such as lungs, pancreas, liver or intestines. Particularly useful is porcine intestinal mucosa, which after proteolysis is treated with ion exchanger, after which the ion exchanger is eluted with aqueous salt solutions, which are preferably sodium chloride solutions. To afford a preliminary separation of the product from heparin, the eluate is diafiltered against aqueous salt solutions in an apparatus with a nominal cutoff of a relative molecular mass of 10000, and preferably of about 5500 daltons, after which the product obtained is bound to ion exchanger, the ion exchanger is eluted with aqueous salt solutions and precipitated with organic solvents, usually by means of solvents miscible with water such as alcohols, and preferably methanol, and if required further purified from nucleic acids by for example bleaching, sodium hydroxide treatment, RNAse treatment, manganese dichloride treatment and/or precipitation, optionally followed by treatment with a solution of potassium permanganate. The precipitation is preferably performed in a fractional way by means of gradually increasing amounts of methanol in water.

The new product, although not containing heparin or heparin fractions, can be processed in the manner conventionally employed for heparin into a pharmaceutical dosage form, e.g. by dissolution in water suitable for injection purposes, to which if required further pharmaceutically acceptable auxiliaries are added.

Clinical application is by means of subcutaneous or intravenous injection or by infusion. Other methods of dosing are also possible, such as intra-pulmonary application via spray inhalation or administration by means of a suppository.

The following examples serve to illustrate the invention.

EXAMPLE 1

Preparation of Batch I

1. Isolation of the crude product

Stabilized mucosa is digested by a proteolytic enzyme at elevated temperature and at an alkaline pH. The digested mixture is treated for 12–16 h with an anion exchanger, to which the active material is bound. The ion exchanger with bound active material is eluted with a NaCl solution in tap water.

The eluate is concentrated about 10× and diafiltrated against 5 volumes of NaCl (about 2%) in tap water, in an ultrafiltration apparatus equipped with membranes with a nominal weight cutoff of a relative molecular mass of about 5500 D.

This permeate and diafiltrate contain the final product and is the starting material for the isolation procedure.

The permeate and diafiltrate are mixed and subsequently diluted with tap water to enable a readsorption of product to an ion exchanger. The ion exchanger with bound active material is washed with tap water. The ion exchanger is eluted with an 11% NaCl solution.

The desired product is obtained by fractional precipitation with methanol and precipitates between 60 and 75% methanol.

The washed residue is dried under reduced pressure at 40°±5° C.

Nucleic acids are removed by bleaching of the crude product, followed by fractioned precipitation between 60 and 75% methanol.

2. KMnO₄ purification

The obtained partly purified product is dissolved in distilled water. The aqueous solution collected is rapidly heated to 60° C. and the pH is adjusted to 9.5. A sodium permanganate solution (40%, w/v) is added to the hot solution after which the solution is kept at 60° C. for 1 h. The solution is then cooled to 20° C. The manganese dioxide formed is removed by filtering through a sterilized filter and the filtrate is brought to pH 6.0. The product is precipitated with 2% (w/w) NaCl and successively with 75 and 90% methanol.

The material is stored in tightly closed aluminium containers.

| Specifications | |
|---|---|
| average molecular weight | 5270 |
| nitrogen | 2.6% |
| sulphur | 8.3% |
| sodium | 9.8% |
| dermatan sulphate | 11.6% |
| chondroitin sulphate | 4.6% |
| anti-Xa activity u/mg | 16.7 |
| antithrombin act. u/mg | 0.13 |

EXAMPLE II

Porcine intestinal mucosa is treated with proteolytic enzymes from porcine pancreas. After 15 h at pH 8.5 the solution is filtered and brought into contact with a strong alkaline ion exchanger for 15 h. Next, the ion exchanger is separated from the liquid and absorbed glycosaminoglycans are eluted with an aqueous solution of sodium chloride (200 g/l).

The eluate is concentrated and diafiltered using an ultrafiltration filter with a nominal molecular weight cut-off at 5500 daltons.

The permeate-diafiltrate fractions are combined and the crude glycosaminoglycan mixture is readsorbed onto a strongly basic ion exchanger. After washing the resin, glycosaminoglycans are eluted at 11% sodium chloride, and the crude product is obtained by fractional precipitation with methanol at 50% and 75%. Further purification is achieved by repeated fractional precipitation with methanol, followed by an oxidation step with 1% hydrogen peroxide at pH 10 and precipitation with 75% methanol.

EXAMPLE III

Porcine intestinal mucosa is digested with proteolytic enzymes from Bacillus subtilis at 35° C. and pH 8.2 for 24 h. After filtration, crude powder was obtained by adsorption to a basic ion exchanger, elution with an aqueous solution of 20% sodium chloride, and fractional precipitation with methanol between 50 and 75%.

The material is redissolved in water containing 2% sodium chloride, ultrafiltered and diafiltered through a filter with a molecular weight cut-off of nominally 5500 daltons. Permeate and diafiltrate are combined and the glycosaminoglycans are adsorbed to an anion exchanger. After washing, the resin is eluted with 11% sodium chloride. The glycosaminoglycan fraction of this eluate is precipitated with 75% methanol and further processed as described in Example I.

EXAMPLE IV

In an analogous manner as described in Example I batches II–VI were prepared from different sources of porcine intestinal mucosa.

| Specifications | Batch | | | | |
| --- | --- | --- | --- | --- | --- |
|  | II | III | IV | V | VI |
| average molecular weight | 5610 | 4940 | 6100 | 5130 | 5320 |
| nitrogen | 2.6% | 2.6% | 2.6% | 2.6% | 2.6% |
| sulphur | 8.4% | 8.0% | 8.2% | 8.4% | 8.4% |
| sodium | 9.8% | 9.5% | 9.9% | 9.9% | 9.8% |
| dermatan sulphate | 10.3% | 8.4% | 11.2% | 11.1% | 10.3% |
| chondroitin sulphate | 7.0% | 6.8% | 4.7% | 6.6% | 3.5% |
| anti-Xa activity u/mg | 16.2 | 14.0 | 16.4 | 15.1 | 16.1 |
| antithrombin act. u/mg | <0.1 | 0.1 | 0.2 | 0.2 | 0.3 |

We claim:

1. Sulphated glycosaminoglycuronan having antithrombotic activity, which is essentially free of heparin, comprising salts of dermatan sulphate in an amount of from 5% to 25% by weight, chondroitin sulphate in an amount of from 0% to 9% by weight and heparan sulphate in an amount of from 66% to 95% by weight, wherein the sulphated glycosaminoglycuron has
   a) an average molecular weight between 4000 and 8000 daltons;
   b) a nitrogen content between 2.4 and 3.0%;
   c) a sulphur content between 7.5 and 9.5%;
   d) a sodium content between 9 and 11%;
   e) an anti-Xa activity between 11 and 20 units/mg; and
   f) an antithrombin III dependent antithrombin activity of less than 1 unit/mg.

2. Process for the manufacture of sulphated glycosaminoglycuronan that is essentially free of heparin, comprising breaking down mammalian tissue by enzyme lysis, contacting the product of enzyme lysis with an anion exchanger to bind sulphated glycosaminoglycuronan containing active material, and eluting said active material from the anion exchanger with aqueous salt solution, whereby preliminary separation from heparin is effected, thereafter diafiltering the eluate against an aqueous salt solution using an apparatus with a nominal cutoff of no greater than 10,000 daltons, binding the diafilter product to an anion exchanger, eluting with an aqueous salt solution and precipitating with an organic solvent that is miscible with water.

3. Process according to claim 2, wherein porcine intestinal mucosa is digested by proteolytic enzymes, the aqueous salt solutions are solutions of sodium chloride, the diafiltration is performed in an apparatus with a nominal cutoff of a relative molecular mass of about 5500 daltons, and the precipitation is performed with gradually increasing amounts of methanol in water.

4. Pharmaceutical composition comprising pharmaceutically acceptable auxiliaries and an effective amount of sulphated glycosaminoglycuronan according to claim 1 to provide antithrombotic activity.

* * * * *